(12) United States Patent
Magne-Drisch et al.

(10) Patent No.: US 6,369,287 B1
(45) Date of Patent: *Apr. 9, 2002

(54) PROCESS FOR CO-PRODUCTION AND SEPARATION OF ETHYLBENZENE AND PARAXYLENE

(75) Inventors: Julia Magne-Drisch, Vilette de Vienne; Gérard Hotier, Rueil Malmaison; Fabio Alario, Neuilly sur Seine; Alain Methivier, Orleans, all of (FR)

(73) Assignee: Institut Francais du Petrole, Rueil Malmaison Cedex (FR)

( * ) Notice: Subject to any disclaimer, the term of this patent is extended or adjusted under 35 U.S.C. 154(b) by 0 days.

This patent is subject to a terminal disclaimer.

(21) Appl. No.: 09/597,468

(22) Filed: Jun. 19, 2000

(30) Foreign Application Priority Data

Jun. 17, 1999 (FR) .............................. 99 07806

(51) Int. Cl.[7] .............................. C07C 7/00; C07C 7/12
(52) U.S. Cl. .................. 585/805; 585/822; 585/825; 585/828
(58) Field of Search ............... 585/805, 822, 585/825, 828

(56) References Cited

U.S. PATENT DOCUMENTS 4,537,754 A * 8/1985 Casci et al. ............... 423/277
5,284,992 A    2/1994 Hotier et al. ............... 585/805
6,177,604 B1 * 1/2000 Hotier et al. ............... 585/805

FOREIGN PATENT DOCUMENTS

| EP | 0 051 318 | 5/1982 |
| FR | 2 772 752 | 6/1999 |
| FR | 2 773 149 | 7/1999 |

* cited by examiner

Primary Examiner—Walter D. Griffin
Assistant Examiner—Tam M. Nguyen
(74) Attorney, Agent, or Firm—Millen, White, Zelano & Branigan, P.C.

(57) ABSTRACT

A process for co-production of paraxylene and ethylbenzene comprises: (A) an adsorption stage of a feedstock of xylenes and ethylbenzene in a simulated moving bed that produces an extract of pure paraxylene and an ethylbenzene-rich raffinate; (B) an adsorption stage in a simulated moving bed, of raffinate from which desorbent has been removed that supplies an essentially pure ethylbenzene extract and an orthoxylene and metaxylene raffinate that contains desorbent; (C) a recover stage for the desorbent; (D) an isomerization stage for the orthoxylene and metaxylene raffinate in the presence of a catalyst that comprises an EUO-type zeolite; and (E) a stage for recycling the isomerate that is produced with adsorption.

20 Claims, 1 Drawing Sheet

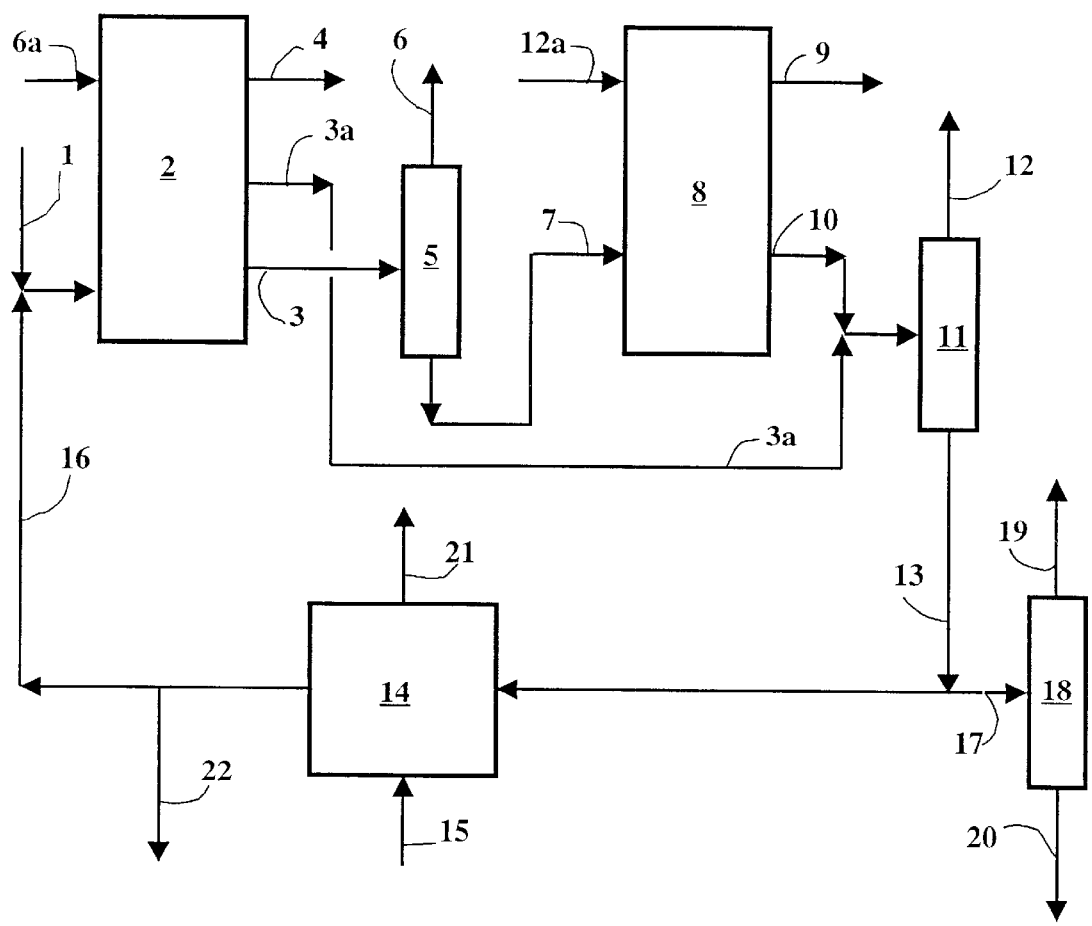

PROCESS FOR CO-PRODUCTION AND SEPARATION OF ETHYLBENZENE AND PARAXYLENE

The invention relates to a process for co-production of paraxylene and ethylbenzene from an aromatic hydrocarbon feedstock that contains isomers with 8 carbon atoms.

The invention applies particularly to the synthesis of very pure paraxylene for producing a petrochemical intermediate product, terephthalic acid.

The prior art is illustrated by Patent Application FR-A-2 773 149.

The production and separation of paraxylene are carried out in industrial practice by arranging the following in a loop:

a process for separation of the paraxylene by adsorption (U.S. Pat. No. 2,985,589, U.S. Pat. No. 3,626,020), whose effluents are paraxylene, on the one hand, and an aromatic C8 fraction that is substantially free of paraxylene, on the other hand. Crystallization can be combined with the adsorption stage to obtain paraxylene that is more pure (U.S. Pat. No. 5,284,992, U.S. Pat. No. 5,401,476);

a process for isomerizing the aromatic C8 fraction that treats the second of the two effluents of the separation unit and produces an isomerate that contains paraxylene. This isomerate is recycled to the feedstock stream that feeds the paraxylene separation unit.

There are two classes of processes for isomerization of aromatic compounds with eight carbon atoms: the first class is known under the name "converting isomerization" because ethylbenzene is in part converted into xylenes, which are in proportions that are close to those of the thermodynamic equilibrium. The catalysts that are used in the converting isomerization steps are bifunctional. A catalyst with a zeolite base ensures the conversion of orthoxylenes and metaxylenes into paraxylene by migration of the methyl groups. As a result, at the temperature in question, thermodynamic equilibrium is nearly reached among the three xylenes: at 400° C., typically, orthoxylene 24%, metaxylene 52%, and paraxylene 24%. Dispersed platinum ensures, in the presence of hydrogen, a hydrogenating-dehydrogenating function that makes it possible to convert the ethylbenzene into a mixture of xylenes. Hydrogen is necessary for producing the naphthenic intermediate products that yield xylenes after dehydrogenation.

The operating conditions of the isomerization are often dictated by the conversion of ethylbenzene: temperature and partial hydrogen pressure. The intermediate reactions for conversion of the ethylbenzene lead to the presence of a significant proportion of naphthenes in the loop. The applied temperature is increased to ensure the desired paraxylene production. Taking into account the compositions of the fresh feedstock and of the isomerate, it is necessary to treat the flow of fresh feedstock 3 to 5 times in the separation unit to produce about 0.85 times the flow of fresh feedstock in the form of paraxylene. The 5 to 10% of fresh feedstock that is not converted into paraxylene is found in the form of cracking and transalkylation products.

The second class of isomerization processes is known under the name of dealkylating isomerization.

In this type of isomerization, ethylbenzene is converted into benzene and ethylene on catalysts with a ZSM5 zeolite base, while the xylenes are brought into thermodynamic equilibrium. Hydrogen is also needed here to hydrogenate into ethane the ethylene that is formed (to prevent realkylation) and to prevent the coking of the catalyst. The $H_2$/HC ratio, however, is considerably lower than that found in converting isomerization. In this case, co-production in the separation-isomerization loop of paraxylene (about 78%) and benzene (15%), with 7% of various losses, is ensured. Here again, the temperature conditions are still dictated by the fact that it is necessary to dealkylate the ethylbenzene.

In contrast, in industrial practice, ethylbenzene is the reaction intermediate product that makes it possible to obtain styrene by dehydrogenation. Ethylbenzene is always produced by alkylation of benzene with ethylene. These alkylation units require a reactor with considerable recycling to be able to control the exothermicity of the reaction and, moreover, a number of distillations finally to separate gases, benzene, ethylbenzene, and di-, tri- and tetraethylbenzene.

Molecular sieves that can separate ethylbenzene from xylenes have been described effectively (Patents U.S. Pat. No. 4,497,972, U.S. Pat. No. 5,453,560). Despite the respectable separation performance levels of these sieves, to our knowledge no commercial unit for separation of ethylbenzene in a simulated moving bed has been built to date.

The prior art actually has always regarded the production of ethylbenzene as an isolated problem. If it is considered that the aromatic C8 feedstocks from which ethylbenzene is to be extracted contain at most 16%, a process for separating ethylbenzene, such as, for example EBEX$^{(R)}$, is more expensive than a unit for alkylating benzene. This way of looking at things has quite often been reinforced by the fact that the locations where paraxylene and orthoxylene, on the one hand, and those of styrene, on the other, are produced are generally geographically different: actually, the xylene production line is most often integrated into a refinery to keep from having to transport the aromatic C8 fraction. In some cases, however, it is integrated into a plant for producing terephthalic acid or methyl terephthalate. By contrast, the ethylbenzene production line is generally integrated into a plant for producing styrene and polystyrene.

An object of the invention is to eliminate the drawbacks that are mentioned above.

Another object is the co-production of ethylbenzene and paraxylene.

Another object is the improvement of the performance levels of the aromatic loop with the use of an isomerization catalyst that comprises an EUO-structural-type zeolite that preferably contains the EU-1 zeolite.

Another object relates to the analogous production of essentially pure metaxylene and orthoxylene when the intent is not to maximize the production of paraxylene.

It has been observed that by combining a first adsorption step, from which an ethylbenzene-rich raffinate was drawn off, with a second adsorption step of this raffinate, from which a fraction that is very low in ethylbenzene and that contains orthoxylene and metaxylene that have been subjected to isomerization under favorable conditions would be drawn off, very good results under very economical conditions were obtained.

More specifically, the invention relates to a process for co-production of paraxylene and ethylbenzene from an aromatic hydrocarbon feedstock (1) that contains isomers with 8 carbon atoms, in which in the presence of a first desorbent (6*a*), said feedstock is brought into contact with a zeolitic adsorbent in a first adsorption unit (2) in a simulated moving bed; a first paraxylene-rich fraction (4) and a second fraction (R1) (3) that is low in paraxylene and high in ethylbenzene are drawn off; said second fraction (R1) is brought into contact with a second suitable adsorbent in a second adsorption unit (8) in a simulated moving bed in the presence of a second desorbent (12a); a third fraction (9) that comprises essentially pure ethylbenzene and a fourth orthoxylene-rich and metaxylene-rich fraction (10) that essentially no longer contains ethylbenzene are recovered; at least a portion of the fourth fraction is isomerized in an isomerization zone (14) in the presence of a catalyst that comprises an EUO-structural-type zeolite; an isomerate (16) is collected, and it is recycled in first adsorption unit (2).

The two adsorption units are generally used according to the simulated moving-bed technique.

According to an advantageous characteristic of the process, it is possible to determine an additional chromatographic zone in first adsorption unit (2) by using five zones instead of four, for example. Said zone is introduced downstream from the draw-off of second fraction (R1) so as to collect the second fraction with a minimal first desorbent content, and downstream from said chromatographic zone, another fraction R2 (3a) is drawn off that is low in paraxylene and high in orthoxylene and metaxylene but essentially no longer contains ethylbenzene, and at least a portion of said fraction (R2) is isomerized in isomerization zone (14).

The invention offers the following advantages:

The productivity of the separation process of paraxylene in the first adsorption unit is improved because the recycling of the isomerate that contains very little ethylbenzene in said unit leads to a reduction in the concentration of ethylbenzene of the adsorption feedstock, the productivity of the process for separation of ethylbenzene in the second adsorption unit is improved because of the absence of paraxylene in the feedstock of said unit, the use of a catalyst that comprises an EUO-structural-type zeolite in the isomerization zone makes it possible to improve the performance levels and also to increase the yield per pass of paraxylene, i.e., the recycling rate is lower, the isomerization feedstock volume is lower and the catalyst volume that is used for the isomerization is reduced, the absence of ethylbenzene in the isomerization feedstock makes it possible to operate the isomerization unit under much less rigorous conditions than conventional units (a temperature of less than 20 to 30° C., low hydrogen pressure) and with better productivity (hourly volumetric flow rate greater than 20 to 50%). As a result, the production of undesirable by-products is avoided, unlike the converting and dealkylating isomerizations of the prior art, finally, by producing at the outlet of the first adsorption unit two fractions (raffinates, for example), of which one that is very concentrated in ethylbenzene becomes the feedstock for the second adsorption unit, the size of said unit is reduced while its productivity is increased.

It is possible to distill the second R1 ethylbenzene-containing fraction to eliminate at least a portion of the first desorbent and to recover the ethylbenzene-containing fraction that is introduced into the second adsorption unit for producing the essentially pure ethylbenzene and said fourth fraction that contains essentially metaxylene and orthoxylene.

This fourth fraction can be distilled so as to eliminate at least a portion of the second desorbent before being isomerized under mild conditions.

According to another characteristic of the process, when the draw-off of said raffinate that contains essentially metaxylene and orthoxylene is initiated in the first adsorption unit of fraction R2, it is possible to distill this fraction so as to eliminate at least a portion of the first desorbent, before being isomerized. If it is necessary to do so, it may be advantageous to distill fourth fraction (13, 17) from which desorbent is removed so as to recover an essentially pure metaxylene distillate (19) and an essentially pure orthoxylene residue (20).

It becomes very advantageous to distill the first and second desorbents in the same distillation column when, quite clearly, the first and second desorbents are identical. This is particularly the case when the operation is carried out with toluene in the two adsorption units or with paradiethylbenzene.

It still remains possible to use a first desorbent in the first adsorption unit that is different from the second desorbent in the second unit.

It is possible to distill fraction (R2) from which the first desorbent is removed so as to recover an essentially pure metaxylene distillate and an essentially pure orthoxylene residue. This distillation can advantageously be carried out in the same distillation column as the one that is used to treat the fourth orthoxylene and metaxylene fraction that is drawn off from the second adsorption unit.

According to a particularly advantageous characteristic, the first adsorption unit and the second adsorption unit use the principle of chromatography in a simulated moving bed, in simulated countercurrent according to U.S. Pat. No. 2,985,589 or with simulated co-current according to U.S. Pat. No. 4,498,991 and U.S. Pat. No. 4,402,832. More specifically, it may be advantageous to operate the first unit under the following conditions:

Simulated countercurrent:
Temperature: 100 to 200° C.
Pressure: 2 to 30 bars (1 bar=$10^5$ Pa)
Desorbent to hydrocarbon-containing feedstock ratio: 1 to 2
Number of beds: 6 to 24
Desorbent: toluene or paradiethylbenzene The adsorbents can be, for example, one of the those that are described in Patents U.S. Pat. No. 3,626,020 and U.S. Pat. No. 3,878,127.

More particularly, an X zeolite that is exchanged with barium and hydrated or a Y zeolite that is exchanged with potassium and barium is used. Toluene or para diethylbenzene will preferably be used as a desorbent.

Of course, the desorbent will be selected based on the adsorbent.

The second adsorption unit for separating ethylbenzene from the mixture that comprises ethylbenzene, metaxylene, and orthoxylene can be operated under the following conditions:

Simulated countercurrent:
Number of beds: 6 to 24
Temperature: 100 to 200° C.
Pressure: 2 to 30 bars
Desorbent: toluene or paradiethylbenzene
Desorbent to feedstock ratio: 1 to 3

The zeolitic adsorbent of the second adsorption unit that feeds ethylbenzene can contain at least one element that is selected from the group of elements K, Rb, Cs, Ba, Ca, and Sr and optionally water. The conditions of this particular adsorption are described in, for example, U.S. Pat. Nos. 5,453,560, 4,613,725, 4,108,915, 4,079,094 and 3,943,182.

Titanosilicate-containing adsorbents that preferably have a pore opening on the order of 8 Å, for example, such as those that are described in U.S. Pat. Nos. 5,244,650, 5,011,591, and U.S. Pat. No. 4,853,202, if the ethylbenzene/metaxylene selectivity is high, allow excellent separation and can provide excellent results.

BRIEF DESCRIPTION OF THE DRAWINGS

The invention will be better understood based on the single figure that diagrammatically illustrates the process.

A feedstock that is provided via a supply line 1 and comprises a mixture of paraxylene, orthoxylene, metaxylene, and ethylbenzene is introduced into a first adsorption unit 2. This unit comprises chromatographic columns that are filled with an adsorbent, a Ba-X zeolite, for example, and it operates according to the principle of a simulated countercurrent moving bed. Said unit comprises four chromatographic zones. A raffinate that consists essentially of orthoxylene and metaxylene and ethylbenzene and desorbent is recovered via a line 3. The desorbent which is toluene that is introduced via a line 6a makes it possible to desorb via a line 4 an extract that consists of essentially pure paraxylene and toluene that is distilled and recycled (not shown in the FIGURE).

The raffinate is sent via line 3 into a distillation column 5 which feeds a toluene distillate via a line 6 that is optionally recycled and a residue. The latter is introduced via a line 7 into a second adsorption unit 8 that operates as first unit 2, according to the principle of the simulated countercurrent moving bed. Said smaller second unit comprises columns that are filled with an adsorbent that contains, for example, titanosilicate. This unit comprises four main chromatographic zones. A raffinate that contains desorbent and metaxylene and orthoxylene is drawn off via a line 10 while an extract that contains basically essentially pure ethylbenzene and desorbent is desorbed by the toluene that is introduced via a line 12a. This draw-off is carried out via a line 9 downstream from the line for introducing desorbent into unit 8.

The raffinate is sent into a distillation column 11 that feeds a toluene distillate via a line 12 and a residue of orthoxylene and metaxylene via a line 13. At least a portion of this residue can be introduced into a distillation unit 18 via a line 17. Said unit 18 makes it possible to recover an essentially pure metaxylene distillate via a line 19 and an essentially pure orthoxylene residue via a line 20. The other portion of the residue is sent into an isomerization unit that operates with or without hydrogen that is introduced via a line 15. This unit contains a catalyst that comprises an EUO-structural-type zeolite. The isomerization is used under conditions of temperature and pressure that are not very severe since the feedstock that is to be isomerized does not contain ethylbenzene. The isomerate that is collected via a paraxylene-enriched line 16 essentially contains no ethylbenzene and is mixed at line 1 of the xylene feedstock of the first adsorption unit. The lightest hydrocarbons are evacuated from the isomerization zone via a line 21. Also, preferably by a standard method that is not shown in the figure, at least some of the C9+ compounds are eliminated from the isomerate.

In the first adsorption unit, it is advantageous to establish five chromatographic zones instead of four, as indicated above. A second raffinate that essentially does not contain ethylbenzene and does contain orthoxylene, metaxylene and a minimal quantity of desorbent is then drawn off upstream from the introduction of the desorbent (line 6a) and downstream from the raffinate (line 3), via a line 3a. This line 3a is connected to line 10 for the introduction of the raffinate into distillation column 11, making it possible to eliminate the desorbent from the mixture of orthoxylene, metaxylene, and toluene.

The conditions of the isomerization stage are generally as follows:

The catalyst that is used within the scope of this invention contains an EUO-structural-type zeolite that is usually in a ratio by weight of about 1% to about 95%, often about 3% to about 70% and most often about 3% to about 50%. The EUO-structural-type zeolite that is contained in the catalyst, in particular the EU1 zeolite, the ZSM50 zeolite or the TPZ-3 zeolite, and their production process are described in the literature, for example, Patent EP-B-42226, U.S. Pat. No. 4,640,829 or EP-A-51318 and in Patent Application FR-A-2 772 752 that is incorporated as a reference. The catalyst is usually in ball form or in extrudate form. The EUO-structural-type zeolite comprises silicon and at least one element T that is selected from the group that is formed by aluminum, iron, gallium and boron, preferably aluminum and boron, whose Si/T atomic ratio is between 5 and 100 inclusive, preferably between 5 and 80 inclusive and preferably also between 5 and 60 inclusive. Said zeolite is at least partly in acid form, i.e., in hydrogen form (H+), whereby the sodium content is such that the Na/T atomic ratio is less than 0.5, preferably less than 0.1, even more preferably less than 0.02, relative to the catalyst, from 0.01 to 10% inclusive, often 0.02 to 5.0% inclusive and preferably 0.05 to 1.0% inclusive by weight, of at least one metal of group VIII of the periodic table (Handbook of Chemistry and Physics, 45th Edition, 1964–1965), preferably selected from the group that is formed by platinum and palladium and even more preferably platinum, whereby said metal of group VIII is deposited on the zeolite or on the binder, preferably selectively on the binder and that usually has a dispersion that is measured by, for example, chemisorption, for example by H2-O2 titration or, for example, by carbon monoxide chemisorption, between 50 and 100% inclusive, preferably between 60 and 100% inclusive and even more preferably between 70 and 100% inclusive. Moreover, the macroscopic distribution coefficient of said metal (s), obtained from its profile that is determined by Castaing microprobe, whereby said distribution coefficient is defined as the ratio of concentrations of said metal in the core of the grain relative to the edge of this same grain, is usually between 0.7 and 1.3 inclusive, preferably between 0.8 and 1.2 inclusive, optionally 0.01 to 2% inclusive and preferably between 0.05 and 1.0% inclusive by weight, of at least one metal from the group that is formed by groups IIIA and IVA of the periodic table, preferably selected from the group that is formed by tin and indium, optionally sulfur whose content is such that the ratio of the number of sulfur atoms to the number of metal atoms of group VIII that are deposited is between 0.5 and 2 inclusive, the make-up to 100% by weight of at least one binder, most often non-zeolitic, such as, for example, alumina, silica, a silica-alumina or any other binder that is conventionally used by ones skilled in the art to produce known isomerization catalysts, preferably of alumina.

This catalyst can also comprise another isomerization catalyst that may or may not be zeolitic of xylenes and/or ethylbenzene.

The process of the invention can be used in liquid phase or in gas phase. In the context of the process according to this invention, it is most often preferred to carry out the isomerization in vapor phase.

The isomerization temperature is between 250 and 500° C., preferably between 300 and 450° C., and even more preferably between 350 and 420° C., and the partial hydrogen pressure is between 3 and 15 bar absolute, preferably between 4 and 12 bar absolute (1 bar=105 Pa) and very often 7 to 12 bar absolute; the total pressure is about 4 to 20 bar absolute, preferably 6 to 15 bar absolute; the PPH (feedstock weight/catalyst weight/hour) is about 0.25 to 10 h-1 and preferably about 1 to 15 h-1, and very often 3 to 6 h-1.

The following example illustrates the invention. It is carried out according to the schematic diagram of FIG. 1.

EXAMPLE

The fresh aromatic hydrocarbon feedstock (line 1) has the following composition:
Toluene: 1.0
Ethylbenzene: 15.0
P-xylene: 21.0
M-xylene: 42.0
O-xylene: 20.0
$C_9+$: 1.0

The mixture of aromatic compounds with 8 carbon atoms that is obtained from the effluent of the recycled isomerization zone (line 16) has the following composition (% by weight):
Toluene: 1.1
Naphthenes with 8 carbon atoms: 3.3
Ethylbenzene: 1.2
P-xylene: 22.7
M-xylene: 50.9
O-xylene: 20.6
$C_9+$: 0.2

The mixture that is treated in the zone for separating xylenes (2) consists of 28% by weight of fresh feedstock (line 1) and 72% by weight of aromatic compounds with 8 carbon atoms that are obtained from the effluent of the isomerization zone (line 16).

At the inlet of separation zone (2), the feedstock therefore has the following composition (% by weight):
Toluene: 1.1
Naphthenes with 8 carbon atoms: 2.4
Ethylbenzene: 5.1
P-xylene: 22.2
M-xylene: 48.4
O-xylene: 20.4
$C_9+$: 0.4

The first simulated countercurrent moving-bed adsorption, which makes it possible to extract paraxylene, takes place under the following conditions:
Sieve: Ba-X; 5.5% H2O measured by the loss due to ignition (LOI) at 950° C.
Temperature: 160° C.
Number of beds: 24
Minimum pressure: 9 bar
Toluene/feedstock ratio: 1.6:1
Productivity: 72.8 kg of PX/$m^3$ of sieve/hour The paraxylene that is recovered as extract has a 99.8% purity and a 97.4% yield.

After extraction of the paraxylene (line 4), the ethylbenzene-rich raffinate (line 3) is distilled (5) to eliminate the toluene that is used as a desorption solvent. After distillation, the column bottom is sent (line 7) to a second separation zone (8). The feedstock at the inlet of the second simulated countercurrent moving bed therefore has the following composition (% by weight):
Toluene: 0.95
Naphthenes with 8 carbon atoms: 3.2
Ethylbenzene: 6.5
P-xylene: 0.6
M-xylene: 62.0
O-xylene: 26.2
$C_9+$: 0.55

The second simulated countercurrent moving-bed adsorption that makes it possible to extract ethylbenzene takes place under the following conditions:
Sieve: Titanosilicate
Temperature: 160° C.
Number of beds: 18
Minimum pressure: 9 bar
Toluene/feedstock ratio: 1.6:1
Productivity: 30 kg of ethylbenzene/$m^3$ of sieve/hour The ethylbenzene that is recovered as extract has a 99% purity and a 95% yield.

After the ethylbenzene is extracted (line 9), the ortho- and metaxylene-rich raffinate (line 10) is distilled (11) to eliminate the toluene that is used as a desorption solvent via line (12). After distribution, the column bottom is sent (line 13) to isomerization reactor (14).

The feedstock at the inlet of the isomerization reactor therefore has the following composition (% by weight):
Toluene: 1.0
Naphthenes with 8 carbon atoms: 3.3
Ethylbenzene: 0.4
P-xylene: 0.6
M-xylene: 66.1
O-xylene: 27.9
$C_9+$: 0.6

This feedstock is isomerized in isomerization reactor (14) under the following conditions:
Catalyst: Pt/EU-1 zeolite with the Si/Al atomic ratio=18/binder (alumina) (0.3%/10%/89.7%)
Temperature: 380° C.
PPH: 3.5 h-1
H2/hydrocarbon ratio: 4:1
Pressure: 7 bar The isomerization effluent has the following composition (% by weight):
Benzene and light hydrocarbons: 0.5
Toluene: 1.1
Cyclic and non-cyclic saturated compounds with 8 carbon atoms: 3.4
Ethylbenzene: 1.1
p-Xylene: 22.5
m-Xylene: 50.3
o-Xylene: 20.3
$C_9+$: 0.8

The content of aromatic compounds with eight carbon atoms in the effluent is 94.2% by weight.

After the light compounds (line 21) and the C9+ compounds (line 22) are eliminated, the isomerization effluent (line 16), whose composition is explained at the beginning of the example, is recycled at the inlet of first separation zone (2).

The preceding examples can be repeated with similar success by substituting the generically or specifically described reactants and/or operating conditions of this invention for those used in the preceding examples. Also, the preceding specific embodiments are to be construed as merely illustrative, and not limitative of the remainder of the disclosure in any way whatsoever.

The entire disclosure of all applications, patents and publications, cited above and below, and of corresponding French application 99/07.806 are hereby incorporated by reference.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A process for co-production of paraxylene and ethylbenzene from an aromatic hydrocarbon feedstock that contains isomers with 8 carbon atoms, in which in the presence of a first desorbent, said feedstock is brought into contact with a zeolitic adsorbent in a first adsorption unit in a simulated moving bed; a first paraxylene-rich fraction and a second fraction that is low in paraxylene and high in ethylbenzene are drawn off; said second fraction is brought into contact with a second suitable adsorbent in a second adsorption unit in a simulated moving bed in the presence of a second desorbent; a third fraction that comprises essentially pure ethylbenzene, and a fourth orthoxylene-rich and metaxylene-rich fraction that essentially no longer contains ethylbenzene are recovered; at least a portion of the fourth fraction is isomerized in an isomerization zone in the presence of a catalyst; an isomerate is collected, and it is recycled into first adsorption unit, whereby the process is characterized in that the isomerization catalyst comprises a zeolite selected from the group consisting of EU1 zeolite, ZSM-50 zeolite and TPZ zeolite.

2. A process according to claim 1, wherein the isomerization is carried out under the following conditions:

Temperature of 250° C. to 500° C.,

Total pressure of 4 to 20 bar absolute,

Feedstock weight per catalyst weight per hour (PPH): 0.25 to 10 h−1

Catalyst that contains an acid phase and at least one metal of group VIII, partial hydrogen pressure of 3 to 15 bar absolute.

3. A process according to claim 1, wherein an additional chromatographic zone is introduced into first adsorption unit downstream from the draw-off of second fraction so as to collect the second fraction with a minimal first desorbent content, and another fraction is drawn off downstream from said chromatographic zone that is low in paraxylene and high in orthoxylene and metaxylene but that essentially no longer contains ethylbenzene, and at least a portion of said fraction is isomerized in isomerization zone.

4. A process according to claim 1, wherein said second fraction is distilled to eliminate at least a portion of first desorbent and to recover ethylbenzene-rich fraction that is introduced into second adsorption unit.

5. A process according to claim 1, wherein the fourth fraction is distilled so as to eliminate at least a portion of second desorbent before being isomerized.

6. A process according to claim 3, wherein said another fraction is distilled so as to eliminate at least a portion of the first desorbent before being isomerized.

7. A process according to claim 1, wherein a portion of fourth fraction from which the desorbent is removed is distilled so as to recover an essentially pure metaxylene distillate and an essentially pure orthoxylene residue.

8. A process according to claim 5, wherein the fourth fraction and said another fraction are distilled in same column.

9. A process according to claim 6, wherein a portion of the fraction from which the first desorbent is removed is distilled so as to recover an essentially pure metaxylene distillate and an essentially pure orthoxylene residue.

10. A process according to claim 7, wherein the fourth fraction and said another fraction from which desorbent has been removed are distilled in same column.

11. A process according to claim 1, wherein the second adsorbent contains titanium silicate.

12. A process according to claim 1, wherein the isomerization catalyst contains said zeolite and at least one metal of group VIII of the periodic table in a ratio by weight of about 0.01 to 10% inclusive relative to the catalyst.

13. A process according to claim 1, wherein the catalyst contains said zeolite and platinum.

14. A process according to claim 3, wherein said second fraction is distilled (5) to eliminate at least a portion of first desorbent (6a) and to recover ethylbenzene-rich fraction (7) that is introduced into second adsorption unit (8).

15. A process according to claim 14, wherein the fourth fraction (10) is distilled in column (11) so as to eliminate at least a portion of said second desorbent before being isomerized.

16. A process according to claim 15, wherein said another fraction is distilled so as to eliminate at least a portion of the first desorbent before being isomerized.

17. A process according to claim 16, wherein a portion of said fourth fraction from which the desorbent is removed is distilled in column (18) so as to recover an essentially pure metaxylene distillate (19) and an essentially pure orthoxylene residue (20).

18. A process according to claim 17, wherein a portion of the fraction from which the first desorbent is removed is distilled in column (18) so as to recover an essentially pure metaxylene distillate and an essentially pure orthoxylene residue.

19. A process according to claim 18, wherein the catalyst contains said zeolite and platinum.

20. A process according to claim 1, wherein said zeolite is a ZSM-50 zeolite or a TPZ zeolite.

* * * * *